United States Patent [19]

Wagner et al.

[11] 4,192,884

[45] Mar. 11, 1980

[54] SUBSTITUTED 4-(((THIENYL)METHYL)-AMINO)BENZOIC ACIDS AND A METHOD FOR TREATING HYPOLIPIDEMIA

[75] Inventors: Eugene R. Wagner, Carmel; Donald P. Matthews, Indianapolis, both of Ind.

[73] Assignee: The Dow Chemical Company, Midland, Mich.

[21] Appl. No.: 915,049

[22] Filed: Jun. 12, 1978

Related U.S. Application Data

[63] Continuation-in-part of Ser. No. 785,467, Apr. 7, 1977, abandoned.

[51] Int. Cl.$^2$ .................. C07D 333/20; A61K 31/38
[52] U.S. Cl. ....................................... 424/275; 549/77; 549/81; 549/82

[58] Field of Search ............... 260/329 AM, 332.2 A; 424/275

[56] References Cited

FOREIGN PATENT DOCUMENTS 7602332 12/1976 Netherlands .

OTHER PUBLICATIONS

Federov, B. P. et al., "Some Azomethines of the Thiophene Series and the Products of Their Reduction with Borohydride", see Chemical Abstracts, vol. 68, (1968), item 104,869k.

*Primary Examiner*—Howard T. Mars
*Assistant Examiner*—L. Hendriksen

[57] ABSTRACT

Halo-substituted 4-(((thienyl)methyl)amino)benzoic acids, the corresponding esters and salts thereof, and a method for lowering serum lipid levels in mammals.

27 Claims, No Drawings

SUBSTITUTED 4-(((THIENYL)METHYL)-AMINO)BENZOIC ACIDS AND A METHOD FOR TREATING HYPOLIPIDEMIA

CROSS-REFERENCE TO RELATED APPLICATION

This application is a continuation-in-part of application Ser. No. 785,467, filed April 7, 1977, now abandoned.

BACKGROUND OF THE INVENTION

The compound 4-(((2-thienyl) methyl) amino)- benzoic acid and the corresponding ethyl ester have been described in Izo. Akad. Nauk SSSR, Ser. Khim. 1967(9), 2049–55 (CA 68:104869K). Although this compound was not shown to have any utility, related compounds described in the Dutch application No. 7,602,332 are shown to have hypolidemic activity. This publication claims a priority date from U.S. patent application Ser. No. 557,550 filed Dec. 3, 1975.

References to other compounds less closely related to those used in the present invention may be found in U.S. Pat. No. 3,257,191; Australian J. Chem. 19(9), 1747–9 (1966); and Uchenye Zapiski Saratov. Univ. 43, 67–74 (1956) (CA 54:9877e).

BRIEF DESCRIPTION OF THE INVENTION

The novel compounds of the present invention and the corresponding esters thereof are represented by the general formula:

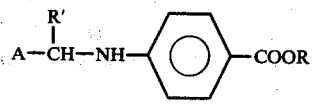

wherein R represents hydrogen or a lower alkyl having from one to about three carbon atoms; R' represents hydrogen or methyl; and A represents halo-substituted thienyl with 1, 2 or 3 halo substitutions being present on the thienyl ring.

As used herein, the term thienyl refers to either 2-thienyl or 3thienyl, with 2thienyl being preferred. The term halo refers to a halogen substitution on the thienyl ring selected from the group consisting essentially of chloro, fluoro and bromo.

Compounds are particularly preferred having the general formula:

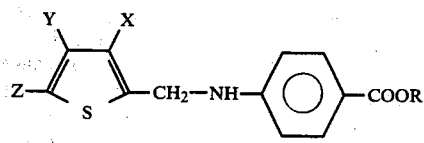

wherein R is as defined above and X, Y and Z independently represent hydrogen or a halo substitution selected from the group consisting essentially of chloro, fluoro or bromo with the proviso that at least one halogen substitution must be present on the thienyl ring.

Pharmaceutically-acceptable salts of the thienyl methyl aminobenzoic acids, i.e. when R is hydrogen, are also considered as being within the scope of this invention. Pharmaceutically-acceptable salts refer to the acid addition salts of those bases which will form a salt with a carboxylic acid and which will not cause an adverse physiological effect when administered to an animal at dosages consistent with good pharmacological activity. Suitable bases thus include, for example, the alkali metal and alkaline earth metal hydroxides, carbonates, and bicarbonates such as sodium hydroxide, potassium hydroxide, calcium hydroxide, potassium carbonate, sodium bicarbonate, magnesium carbonate and the like, ammonia, primary, secondary, and tertiary amines and the like. Also aluminum salts of the instant compound may be obtained by treating the corresponding sodium salt with an appropriate aluminum complex such as aluminum chloride hexahydrate, etc.

The present invention is also directed to a method using the above-described compounds in treating hyperlipidemia in an animal and to hypolipidemic compositions containing a hypolipidemically effective amount of the active compound in combination with a pharmaceutically-acceptable carrier.

DETAILED DESCRIPTION OF THE INVENTION

Compounds of the present invention have shown hypolipidemic activity in animals and in particular in mammals. Hypolipidemic activity as used herein refers to the effect of lowering the blood lipid content and in particular the cholesterol and triglyceride content of the serum. The compounds of the present invention are therefore suitable for use in treating serum hyperlipidemia in mammals and in particular are useful for the treatment of hypercholeslerolemia and hypertriglyceridemica, that is, abnormally high levels of lipids, cholesterol, or triglycerides, respectively, in the serum. The compounds can be administered orally or parenterally by subcutaneous, intravenous, or intraperitoneal injection or by implantation or the like, oral administration being preferred.

The effective hypolipidemic amount of the thienylmethyl aminobenzoic acid compounds to be administered to an animal, that is, the amount which is effective to significantly lower the serum lipid level, can vary depending upon such factors as the animal treated, the particular p-aminobenzoic acid compound employed, the desired lipid level to be obtained, whether or not the animal is hyperlipidemic, the period of administration and the method of administration. In general an effective daily dosage range is from about 1 mg/kg of body weight to 200 mg/kg of body weight, with a daily dosage range of from about 10 mg/kg to 100 mg/kg of body weight being preferred.

For oral administration, pharmaceutical preparations of the thienylmethyl aminobenzoic acids may be made by following the conventional techniques of the pharmaceutical chemist. These techniques involve granulating and compressing when necessary or variously mixing and dissolving or suspending the ingredients as appropriate to the desired end product. Numerous pharmaceutical forms to carry the compounds can be used. For example, the pure compound can be used or it can be mixed with a solid carrier. Generally, inorganic pharmaceutical carriers are preferable and particularly solid inorganic carriers. One reason for this is the large number of inorganic materials which are known to be pharmaceutically safe and acceptable, as well as very convenient in preparing formulations. The compositions may take the form of tablets, linguets, powders, capsules, slurries, troches, or lozenges and such compositions may be prepared by standard pharmaceutical techniques. Tablet compositions may be coated or uncoated and they may be effervescent or non-effervescent. Conventional excipients for tablet formations may be used. For example, inert diluents, such as magnesium carbonate or lactose, disintegrating agents such as maize starch or alginic acid, and lubricating agents such as magnesium stearate may be used.

If a liquid carrier is used, the preparation may be in the form of a soft gelatin capsule, a syrup, a liquid solution or suspension.

The hydrocarbon solubility of most of the compounds of this invention is high enough to allow the use of pharmaceutically-acceptable oils and carriers. For example, vegetable or animal oils such as sunflower oil, safflower oil, maize oil or cod liver oil can be used. Glycerine can also be used. With this, latter solvent from 2 to 30 percent water, may be added. When water alone is the carrier, or when the solubility of the compound in the oil is low, the preparations can be administered in the form of a slurry.

Emulsion compositions may be formulated using emulsifying agents such as sorbitan trioleate, polyoxyethylene sorbitan monooleate, lecithin, gum acacia or gum tragacanth. Aqueous based suspensions may be prepared with the aid of wetting agents such as polyethylene oxide condensation products of alkylphenols, fatty alcohols or fatty acids with the suspending agents, for example, a hydrophilic colloid such as polyvinylpyrrolidone. The emulsions and suspensions may contain conventional excipients such as sweetening agents, coloring materials and preservatives.

The thienylmethyl aminobenzoic acids can also be incorporated in a nutritive foodstuff such as, for example, butter, margarine, edible oils, casein, carbohydrates and the like. Such nutritive compositions are adapted to be administered as a partial or total diet or as a supplement to the diet. Such compositions preferably contain from about 0.02 or less to about 2.0 or more percent of the active ingredient when administered as the total diet. The compositions can contain higher concentrations of the active ingredient when administered as a supplement.

For parenteral use, the compounds of this invention can be formulated with sterile ingredients, compounded and packaged aseptically. They may be administered intravenously or intramuscularly. Useful solvents for formulation in such use are the polyhydric aliphatic alcohols and mixtures thereof. Especially satisfactory are the pharmaceutically acceptable glycols, such as propylene glycol, and mixtures thereof. Glycerine is another example of a polyol which is particularly useful. Up to 25–30 percent by volume of water may be incorporated in the vehicle if desired. An 80 percent aqueous propylene glycol solution is a particularly convenient solvent system. A pH range, about 7.4, and isotonicity compatible with body isotonicity, is desirable. basicity may be controlled by addition of a base as required, and a particularly convenient base is monoethanolamine. It may often be desirable to incorporate a local anesthetic and such are well known to those skilled in the art.

The percentage of the compound to be used in the pharmaceutical carrier may be varied. It is necessary that the compound constitute a proportion such that a suitable dosage will be obtained and it is preferred to use pharmaceutical compositions containing at least 10 weight percent of the compound. Activity increases with concentration of the agent in the carrier, but those compositions containing a significant amount of carrier, e.g. at least 1 percent and preferably at least 5 percent, are preferred as they allow for the easier administration of the compound.

DETAILED DESCRIPTION OF THE INVENTION

The active compounds of the present invention are prepared by known procedures. In general, member compounds are made by reacting p-aminobenzoic acid or an ester thereof in an inert solvent with an aldehyde of the organic radical which is sought to be prepared. The resulting Schiff base may be reduced to prepare the corresponding halo-substituted thienylmethylaminobenzoic acid derivative. A convenient method of carrying out this latter procedure involves mixing the Schiff base with an excess of ethanol and water. Dilute aqueous sodium hydroxide optionally can be added to the mixture. Sodium borohydride is added at room temperature and stirred until it dissolves. The mixture is then heated, poured onto ice, and acidified. The product may be filtered off as a precipitate and further purified by known procedures.

Several of the halogenated aldehydes were not readily available and were prepared by methods generally known from the literature. For example, 4-chloro-2-thiophenecarboxaldehyde was prepared by the chlorination of 2-thiophenecarboxaldehyde using a large excess of the aluminum chloride catalyst. See *J. Org. Chem*, 21 381 (1956) and *J. Heter. Chem.*, 393 (1976). Using the same method 4,5-dichloro-2-thiopenecarboxaldehyde was also prepared from 5-chloro-2-thiophenecarboxaldehyde. See CA 57:16527i.

The following examples will serve to further illustrate the invention, but are not to be construed as a limitation thereon.

EXAMPLE 1

4-(((3,5-dichloro-2-thienyl)methyl)amino)-benzoic acid

A 50% oil dispersion (5.8 grams, 0.12 moles) of sodium hydride was washed with hexane under nitrogen. To this 200 ml of dry dimethylformamide and 29.5 grams (0.113 moles) of solid ethyl N-trifluoroacetylbenzoate was added. The reaction mass exothermed mildly. The mixture was cooled to 20° C. and stirred for 15 minutes. Afterwards, 27.7 grams of 3,5-dichloro-2-bromomethylthiophene was added. The reaction mass was heated for 18 hours at 85° C. At the end of that period the mixture was poured into 1 liter of cold water and extracted with methylene chloride. the product was dried with anhydrous sodium sulfate and the dried solution concentrated to a brown oil. The resulting oil was refluxed for 2 hours with 50 ml of ethanol and 200 ml of 5 N sodium hydroxide. The cooled, brown solution was diluted with water and acidified with acetic acid. The crude 4-(((3,5-dichloro-2-thienyl)methyl)-amino) benzoic acid was obtained as a brown gum and recrystalized from Dowanol PM ® (Dow). The melting point was 169–170.5° C.

EXAMPLE 2

4-(((5-chloro-2thienyl)methyl)amino)-benzoic acid

A mixture containing 46.6 grams (0.34 moles) of p-aminobenzoic acid, 50 grams (0.34 moles) of 5-chloro-2-thiophenecarboxaldehyde and 400 ml. of toluene was heated to reflux for about three and a half hours. The water formed was collected in a Dean-Stark trap. The reaction mass was cooled at the end of this period and the Schiff base collected as a tan solid. To a mixture of the intermediate Schiff base and 1.2 liters of glacial acetic acid 21.2 grams (0.36 moles) of dimethylaminoborane was added. The reaction mass was warmed to 40° C. for about 30 minutes and poured in 2 liters of ice water. The white precipitate of 4-(((5-chloro-2-thienyl)methyl)amino)benzoic acid was washed in water, dried, and recrystallized from toluene. The melting point was 177°–178° C.

EXAMPLE 3

4-(((4,5-dichloro-2-thienyl)methyl)amino)benzoic acid

Step 1: Synthesis of 4,5-dichloro-2-thiophenecarboxaldehyde.

To a mechanically stirred solution of 31.8 grams (0.217 mole) 5-chloro-2thiophenecarboxaldehyde in 150 ml of methylene chloride, 65 grams (0.487 mole) of anhydrous aluminum chloride was added in small portions. The mixture exothermed and turned purple. To this mixture 20.6 grams (0.29 mole) of chlorine in 250 ml of carbon tetrachloride was added dropwise. The reaction mass was refluxed for about 15 hours, and an additional 15 grams (0.21 mole) of chlorine in 200 ml of carbon tetrachloride was added. The mixture was refluxed for an additional 7 hours. The reaction was quenched by pouring over one liter of ice water. The aqueous layer was extracted with chloroform. The chloroform solution was washed with water and sodium bicarbonate. After drying with anhydrous sodium sulfate and concentration under vacuum, a yellow-brown oil was obtained. The crude 4,5-dichloro-2-thiophenecarboxaldehyde crystallized on standing and was recrystallized from hexane.

Step 2: The product 4-(((4,5-dichloro-2-thienyl) methyl)amino)benzoic acid was prepared from the 4,5dichloro-2-thiophenecarboxaldehyde intermediate in essentially the same manner as described in Example 2 above. The melting point was 225°–227° C.

In addition to the compounds described in the examples above other substituted 4-(((2-thienyl)methyl)amino)benzoic acids were prepared using essentially the same techniques. These compounds shown as Examples 4, 5 and 6 were as follows:

EXAMPLE 4

4-(((5-chloro-2-thienyl)methyl)amino)benzoic acid ethyl ester was prepared from ethyl p-aminobenzoate and 5-chloro-2-thiophenecarboxaldehyde. Melting point was 108°–109° C.

EXAMPLE 5

4-(((5-bromo-2-thienyl)methyl)amino)benzoic acid. Melting point was 188°–190° C.

EXAMPLE 6

4-(((4-chloro-2-thienyl)methyl)amino)benzoic acid. Melting point was 165°–168° C.

EXAMPLE 7

4-((1-(5-chloro-2-thienyl)ethyl)amino)benzoic acid. Melting point was 155°–157° C.

EXAMPLE 8

4-(((2-chloro-3-thienyl)methyl)amino)benzoic acid. Melting point was 152°–153° C.

EXAMPLE 9

4-(((2,5-dichloro-3-thienyl)methyl)amino)benzoic acid. Melting point was 195°–197° C.

The structure of the compounds in all of the above examples was confirmed by IR spectra and elemental analysis.

EXAMPLE 10

The hypolipidemic effect of the compounds of the invention was illustratively demonstrated in rats. In this procedure an active compound as herein disclosed was dissolved in acetone, taken up on a silica gel and mixed with normal ground feed to yield concentrations of 0.125 percent of the compound in the animal feed. The treated feed was administered to male rats weighing 150–160 grams over a fourteen day period. Following the fourteen day feeding period, the rats were sacrificed, and the blood samples were collected. The liver was removed, weighed, and frozen for future analysis. The relative levels of serum cholesterol in the blood samples were determined by the Henly method. A. A. Henly, Analyst, 82, 286 (1957), Liver cholesterol was measured by the Sperry-Webb method. *Journal of Biological Chemistry* 187, 97 (1950). The relative levels of triglycerides in the blood and liver samples were determined by the Von Handel and Zilversmit method. *J. Lab. Clin. Med.* 50, 152 (1957) and *Clin. Chem.* 7, 249 (1961). Taking the average levels of the control rats as standard, the mean results obtained in the treated groups is thereby ascertained.

The data presented in Table I summarizes the results of the above studies.

Table I

| Compound Example No. | Serum Cholesterol* | Serum Triglycerides* | Liver Cholesterol* | Liver Triglycerides* | Body Weight* | Liver Weight* |
|---|---|---|---|---|---|---|
| 1 | −31 | −45 | −3 | +2 | 0 | +16 |
| 2 | −34 | −58 | +7 | −14 | −3 | +8 |
| 3 | −43 | −56 | −3 | −39 | −2 | +11 |
| 4 | −42 | −61 | +8 | −8 | −5 | +2 |
| 5 | −30 | −54 | +17 | −11 | −1 | +10 |
| 6 | −35 | −60 | +14 | −14 | −6 | +20 |
| 7 | −15 | −59 | +3 | −16 | +11 | −7 |
| 8 | −23 | −31 | +3 | +3 | −5 | 0 |
| 9 | −20 | −49 | +7 | +14 | −1 | +14 |

*All data represent percent change in values for the treated animals when compared to the control group.

The data in Table I indicate that the compounds of the present invention are highly effective as hypolipidemic agents in the lowering of serum cholesterol and serum triglycerides while causing only minimal changes in liver weight and overall body weight. The compounds 4-(((4,5-dichloro-2-thienyl)methyl)amino)benzoic acid (Example 3) and 4-(((5-chloro-2-thienyl)methyl)amino)benzoic acid ethyl ester (Example 4) are shown to be especially useful in lowering cholesterol levels in mammals. Likewise the compounds 4-(((5-chloro-2-thienyl)methyl)amino)benzoic acid ethyl ester (Example 4) and 4-(((4-chloro-2-thienyl)methyl)amino)benzoic acid (Example 6) were found to be particularly effective in lowering serum triglycerides.

We claim:

1. A compound of the formula:

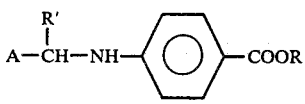

wherein R represents hydrogen or a lower alkyl having from one to about three carbon atoms; R' represents hydrogen or methyl; and A represents halo-substituted thienyl with 1, 2 or 3 halo substitutions being present on the thienyl ring and further including the pharmaceutically-acceptable salts thereof.

2. The compound of claim 1 represented by the formula:

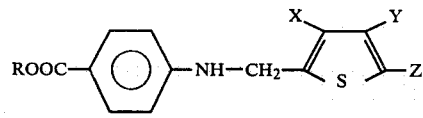

wherein R represents hydrogen or a lower alkyl having from one to about three carbon atoms and X, Y, and Z independently represent hydrogen or a halo substitution selected from the group consisting of chloro and bromo with the proviso that at least one halogen substitution must be present on the thienyl ring and further including the pharmaceutically-acceptable salts thereof.

3. The compound of claim 2 which is 4-(((3,5-dichloro-2-thienyl)methyl)amino)benzoic acid and the pharmaceutically-acceptable salts thereof.

4. The compound of claim 2 which is 4-(((5-chloro-2-thienyl)methyl)amino)benzoic acid and the pharmaceutically-acceptable salts thereof.

5. The compound of claim 2 which is 4-(((4,5-dichloro-2-thienyl)methyl)amino)benzoic acid and the pharmaceutically-acceptable salts thereof.

6. The compound of claim 2 which is 4-(((5-bromo-2-thienyl)methyl)amino)benzoic acid and the pharmaceutically-acceptable salts thereof.

7. The compound of claim 2 which is 4-(((4-chloro-2-thienyl)methyl)amino)benzoic acid and the pharmaceutically-acceptable salts thereof.

8. The compound of claim 2 wherein R is a lower alkyl.

9. The compound of claim 8 which is 4-(((5-chloro-2-thienyl)methyl)amino)benzoic acid ethyl ester.

10. A method for lowering serum lipid levels in a mammal which comprises administering internally to the mammal an effective hypolipidemic amount of a compound having the formula:

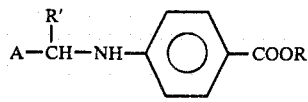

wherein R represents hydrogen or a lower alkyl having from one to about three carbon atoms; R' represents hydrogen or methyl; and A represents halo-substituted thienyl with 1, 2 or 3 halo substitutions being present on the thienyl ring and further including the pharmaceutically-acceptable salts thereof.

11. The method of claim 10 wherein the compound is 4-(((3,5-dichloro-2-thienyl)methyl)amino)benzoic acid and the pharmaceutically-acceptable salts thereof.

12. The method of claim 10 wherein the compound is 4-(((5-chloro-2-thienyl)methyl)amino)benzoic acid and the pharmaceutically-acceptable salts thereof.

13. The method of claim 10 wherein the compound is 4-(((4,5-dichloro-2-thienyl)methyl)amino)benzoic acid and the pharmaceutically-acceptable salts thereof.

14. The method of claim 10 wherein the compound is 4-(((5-bromo-2-thienyl)methyl)amino)benzoic acid and the pharmaceutically-acceptable salts thereof.

15. The method of claim 10 wherein the compound is 4-(((4-chloro-2-thienyl)methyl)amino)benzoic acid and the pharmaceutically-acceptable salts thereof.

16. The method of claim 10 wherein R of the compound is a lower alkyl.

17. The method of claim 16 wherein the compound is 4-(((5-chloro-2-thienyl)methyl)amino)benzoic acid ethyl ester.

18. The method of claim 10 wherein the mammal is hypercholesterolemic.

19. The method of claim 10 wherein the mammal is hypertriglyceridemic.

20. A hypolipidemic composition comprising a suitable pharmaceutical carrier and an effective hypolipidemic amount of a compound having the formula:

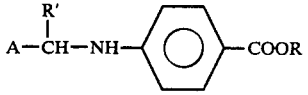

wherein R represents hydrogen or a lower alkyl having from one to about three carbon atoms; R' represents hydrogen or methyl; and A represents halo-substituted thienyl with 1, 2 or 3 halo substitutions being present on the thienyl ring and further including the pharmaceutically-acceptable salts thereof.

21. The composition of claim 20 wherein the compound is 4-(((3,5-dichloro-2-thienyl)methyl)amino)benzoic acid and the pharmaceutically-acceptable salts thereof.

22. The composition of claim 20 wherein the compound is 4-(((5-chloro-2-thienyl)methyl)amino)benzoic acid and the pharmaceutically-acceptable salts thereof.

23. The composition of claim 20 wherein the compound is 4-(((4,5-dichloro-2-thienyl)methyl)amino)benzoic acid and the pharmaceutically-acceptable salts thereof.

24. The composition of claim 20 wherein the compound is 4-(((5-bromo-2-thienyl)methyl)amino)benzoic acid and the pharmaceutically-acceptable salts thereof.

25. The composition of claim 20 wherein the compound is 4-(((4-chloro-2-thienyl)methyl)amino)benzoic acid and the pharmaceutically-acceptable salts thereof.

26. The composition of claim 20 wherein R of the compound is a lower alkyl.

27. The composition of claim 20 wherein the compound is 4-(((5-chloro-2-thienyl)methyl)amino)benzoic acid ethyl ester.

* * * * *